US008554576B1

(12) United States Patent
Reicher et al.

(10) Patent No.: US 8,554,576 B1
(45) Date of Patent: Oct. 8, 2013

(54) AUTOMATED DOCUMENT FILING

(75) Inventors: Murray A. Reicher, Rancho Santa Fe, CA (US); Carol G. Sloyer, La Jolla, CA (US); Cole A. Genovese, Encinitas, CA (US); Christopher S. Franklin, San Diego, CA (US)

(73) Assignee: DR Systems, Inc., San Diego, CA (US)

( * ) Notice: Subject to any disclaimer, the term of this patent is extended or adjusted under 35 U.S.C. 154(b) by 573 days.

(21) Appl. No.: 11/944,027

(22) Filed: Nov. 21, 2007

Related U.S. Application Data

(60) Provisional application No. 60/867,071, filed on Nov. 22, 2006.

(51) Int. Cl.
*G06F 17/00* (2006.01)

(52) U.S. Cl.
USPC ............................................. 705/3; 715/505

(58) Field of Classification Search
USPC .......................................................... 705/3
See application file for complete search history.

(56) References Cited

U.S. PATENT DOCUMENTS

| | | |
|---|---|---|
| 4,672,683 A | 6/1987 | Matsueda |
| 5,123,056 A | 6/1992 | Wilson |
| 5,431,161 A | 7/1995 | Ryals et al. |
| 5,452,416 A | 9/1995 | Hilton et al. |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,852,646 A | 12/1998 | Klotz et al. |
| 5,926,568 A | 7/1999 | Chaney et al. |
| 5,954,650 A | 9/1999 | Saito et al. |
| 5,976,088 A | 11/1999 | Urbano et al. |
| 5,987,345 A | 11/1999 | Engelmann et al. |
| 5,995,644 A | 11/1999 | Lai et al. |
| 6,115,486 A | 9/2000 | Cantoni |
| 6,151,581 A | 11/2000 | Kraftson et al. |
| 6,175,643 B1 | 1/2001 | Lai et al. |
| 6,185,320 B1 | 2/2001 | Bick et al. |

(Continued)

FOREIGN PATENT DOCUMENTS

| | | |
|---|---|---|
| WO | WO 2007/131157 | 11/2007 |

OTHER PUBLICATIONS

Crowley, Rebecca et al., *Development of Visual Diagnostic Expertise in Pathology: an Information-processing Study*, Jan. 2003, Journal of the American medical Informatics Association, vol. 10, No. 1, pp. 39-51.

(Continued)

*Primary Examiner* — Hiep V Nguyen
(74) *Attorney, Agent, or Firm* — Knobbe Martens Olson & Bear LLP

(57) ABSTRACT

A document management device provides a user interface that receives an indication from a user of one or more series associated with an electronic document, such as a scanned or electronically completed medical-related form. In other embodiments, the document management device comprises document detection intelligence that determines a type of document and/or series for an electronic document. After determining a series associated with a document, one or more attributes that have previously been associated with the determined series are associated with the electronic document. The attributes associated with the electronic document may then be used to control user's rights to the document, indicate a type of viewer associated with the document, indicate a storage location for the document, and/or indicate a type of the electronic document, for example.

29 Claims, 8 Drawing Sheets

(56) References Cited

U.S. PATENT DOCUMENTS

| | | | |
|---|---|---|---|
| 6,304,667 B1 | 10/2001 | Reitano | |
| 6,347,329 B1 | 2/2002 | Evans | |
| 6,351,547 B1 | 2/2002 | Johnson et al. | |
| 6,424,996 B1 | 7/2002 | Killcommons et al. | |
| 6,438,533 B1* | 8/2002 | Spackman et al. | 706/45 |
| 6,463,169 B1 | 10/2002 | Ino et al. | |
| 6,532,299 B1 | 3/2003 | Sachdeva et al. | |
| 6,532,311 B1 | 3/2003 | Pritt | |
| 6,556,695 B1 | 4/2003 | Packer et al. | |
| 6,563,950 B1 | 5/2003 | Wiskott et al. | |
| 6,574,629 B1 | 6/2003 | Cooke et al. | |
| 6,577,753 B2 | 6/2003 | Ogawa | |
| 6,603,494 B1 | 8/2003 | Banks et al. | |
| 6,630,937 B2 | 10/2003 | Kallergi et al. | |
| 6,678,764 B2 | 1/2004 | Parvelescu et al. | |
| 6,697,506 B1 | 2/2004 | Oian et al. | |
| 6,775,402 B2 | 8/2004 | Bacus et al. | |
| 6,778,689 B1 | 8/2004 | Aksit et al. | |
| 6,820,100 B2 | 11/2004 | Funahashi | |
| 6,829,377 B2 | 12/2004 | Milioto | |
| 6,864,794 B2 | 3/2005 | Betz | |
| 6,886,133 B2 | 4/2005 | Bailey et al. | |
| 6,891,920 B1 | 5/2005 | Minyard et al. | |
| 6,917,696 B2 | 7/2005 | Soenksen | |
| 6,996,205 B2 | 2/2006 | Capolunghi et al. | |
| 7,022,073 B2 | 4/2006 | Fan et al. | |
| 7,027,633 B2 | 4/2006 | Foran et al. | |
| 7,031,846 B2 | 4/2006 | Kaushikkar et al. | |
| 7,043,474 B2 | 5/2006 | Mojsilovic | |
| 7,050,620 B2 | 5/2006 | Heckman | |
| 7,092,572 B2 | 8/2006 | Huang et al. | |
| 7,103,205 B2 | 9/2006 | Wang et al. | |
| 7,106,479 B2 | 9/2006 | Roy et al. | |
| 7,110,616 B2 | 9/2006 | Ditt et al. | |
| 7,113,186 B2 | 9/2006 | Kim et al. | |
| 7,149,334 B2 | 12/2006 | Dehmeshki | |
| 7,155,043 B2 | 12/2006 | Daw | |
| 7,170,532 B2 | 1/2007 | Sako | |
| 7,174,054 B2 | 2/2007 | Manber et al. | |
| 7,209,149 B2 | 4/2007 | Jogo | |
| 7,212,661 B2 | 5/2007 | Samara et al. | |
| 7,218,763 B2 | 5/2007 | Belykh et al. | |
| 7,224,852 B2 | 5/2007 | Lipton et al. | |
| 7,260,249 B2 | 8/2007 | Smith | |
| 7,263,710 B1 | 8/2007 | Hummel et al. | |
| 7,272,610 B2* | 9/2007 | Torres | 1/1 |
| 7,412,111 B2 | 8/2008 | Battle et al. | |
| 7,450,747 B2 | 11/2008 | Jabri et al. | |
| 7,526,114 B2 | 4/2009 | Seul et al. | |
| 7,545,965 B2 | 6/2009 | Suzuki et al. | |
| 7,583,861 B2 | 9/2009 | Hanna et al. | |
| 7,613,335 B2 | 11/2009 | McLennan et al. | |
| 7,634,121 B2 | 12/2009 | Novatzky et al. | |
| 7,636,413 B2 | 12/2009 | Toth | |
| 7,660,488 B2 | 2/2010 | Reicher et al. | |
| 7,787,672 B2 | 8/2010 | Reicher et al. | |
| 7,920,152 B2 | 4/2011 | Fram et al. | |
| 7,953,614 B1 | 5/2011 | Reicher | |
| 7,970,625 B2 | 6/2011 | Reicher et al. | |
| 8,019,138 B2 | 9/2011 | Reicher et al. | |
| 8,065,166 B2 | 11/2011 | Maresh et al. | |
| 8,094,901 B1 | 1/2012 | Reicher et al. | |
| 8,217,966 B2 | 7/2012 | Fram et al. | |
| 8,244,014 B2 | 8/2012 | Reicher et al. | |
| 8,380,533 B2 | 2/2013 | Reicher et al. | |
| 8,457,990 B1 | 6/2013 | Reicher et al. | |
| 2001/0016822 A1 | 8/2001 | Bessette | |
| 2001/0042124 A1 | 11/2001 | Barron | |
| 2002/0016718 A1 | 2/2002 | Rothschild et al. | |
| 2002/0021828 A1 | 2/2002 | Papier et al. | |
| 2002/0044696 A1 | 4/2002 | Sirohey et al. | |
| 2002/0073429 A1 | 6/2002 | Beane et al. | |
| 2002/0091659 A1 | 7/2002 | Beaulieu et al. | |
| 2002/0103673 A1 | 8/2002 | Atwood | |
| 2002/0103827 A1 | 8/2002 | Sesek | |
| 2002/0110285 A1 | 8/2002 | Wang et al. | |
| 2002/0180883 A1 | 12/2002 | Tomizawa et al. | |
| 2003/0005464 A1 | 1/2003 | Gropper et al. | |
| 2003/0028402 A1 | 2/2003 | Ulrich et al. | |
| 2003/0037054 A1 | 2/2003 | Dutta et al. | |
| 2003/0065613 A1 | 4/2003 | Smith | |
| 2003/0115083 A1 | 6/2003 | Masarie et al. | |
| 2003/0190062 A1 | 10/2003 | Noro et al. | |
| 2003/0204420 A1 | 10/2003 | Wilkes et al. | |
| 2004/0024303 A1 | 2/2004 | Banks et al. | |
| 2004/0086163 A1 | 5/2004 | Moriyama et al. | |
| 2004/0088192 A1 | 5/2004 | Schmidt et al. | |
| 2004/0114714 A1 | 6/2004 | Minyard et al. | |
| 2004/0143582 A1* | 7/2004 | Vu | 707/100 |
| 2004/0161164 A1 | 8/2004 | Dewaele | |
| 2004/0165791 A1 | 8/2004 | Kaltanji | |
| 2004/0243435 A1 | 12/2004 | Williams | |
| 2004/0254816 A1 | 12/2004 | Myers | |
| 2005/0027570 A1 | 2/2005 | Maier et al. | |
| 2005/0043970 A1 | 2/2005 | Hsieh | |
| 2005/0065424 A1 | 3/2005 | Shah et al. | |
| 2005/0108058 A1 | 5/2005 | Weidner et al. | |
| 2005/0114178 A1 | 5/2005 | Krishnamurthy et al. | |
| 2005/0114179 A1 | 5/2005 | Brackett et al. | |
| 2005/0114283 A1 | 5/2005 | Pearson et al. | |
| 2005/0184988 A1 | 8/2005 | Yanof et al. | |
| 2005/0197860 A1 | 9/2005 | Joffe et al. | |
| 2005/0238218 A1 | 10/2005 | Nakamura | |
| 2005/0273009 A1 | 12/2005 | Deischinger et al. | |
| 2006/0031097 A1 | 2/2006 | Lipscher et al. | |
| 2006/0058603 A1 | 3/2006 | Dave et al. | |
| 2006/0093198 A1 | 5/2006 | Fram et al. | |
| 2006/0093199 A1 | 5/2006 | Fram et al. | |
| 2006/0095423 A1 | 5/2006 | Reicher et al. | |
| 2006/0095426 A1 | 5/2006 | Takachio et al. | |
| 2006/0106642 A1 | 5/2006 | Reicher et al. | |
| 2006/0111941 A1 | 5/2006 | Blom | |
| 2006/0181548 A1 | 8/2006 | Hafey | |
| 2006/0230072 A1 | 10/2006 | Partovi et al. | |
| 2006/0241979 A1 | 10/2006 | Sato et al. | |
| 2006/0277075 A1 | 12/2006 | Salwan | |
| 2006/0282408 A1 | 12/2006 | Wisely et al. | |
| 2007/0050701 A1* | 3/2007 | El Emam et al. | 715/505 |
| 2007/0055550 A1 | 3/2007 | Courtney et al. | |
| 2007/0067124 A1 | 3/2007 | Kimpe et al. | |
| 2007/0073556 A1 | 3/2007 | Lau et al. | |
| 2007/0124541 A1 | 5/2007 | Lang et al. | |
| 2007/0162308 A1 | 7/2007 | Peters | |
| 2007/0174079 A1 | 7/2007 | Kraus | |
| 2007/0192140 A1* | 8/2007 | Gropper | 705/3 |
| 2007/0239481 A1 | 10/2007 | DiSilvestro et al. | |
| 2008/0059245 A1 | 3/2008 | Sakaida et al. | |
| 2008/0103828 A1 | 5/2008 | Squilla et al. | |
| 2008/0275913 A1 | 11/2008 | van Arragon et al. | |
| 2009/0129643 A1 | 5/2009 | Natanzon et al. | |
| 2009/0198514 A1 | 8/2009 | Rhodes | |
| 2010/0138239 A1 | 6/2010 | Reicher et al. | |
| 2010/0198608 A1 | 8/2010 | Kaboff et al. | |
| 2010/0201714 A1 | 8/2010 | Reicher | |
| 2011/0016430 A1 | 1/2011 | Fram | |
| 2011/0267339 A1 | 11/2011 | Fram | |
| 2011/0316873 A1 | 12/2011 | Reicher | |
| 2012/0163684 A1 | 6/2012 | Natanzon et al. | |
| 2012/0194540 A1 | 8/2012 | Reicher | |
| 2013/0083023 A1 | 4/2013 | Fram | |

OTHER PUBLICATIONS

Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.

(56) References Cited

OTHER PUBLICATIONS

Non-Final Office Action dated Oct. 1, 2009, in U.S. Appl. No. 11/268,261.
Notice of Allowance dated Feb. 2, 2010, in U.S. Appl. No. 11/268,261.
Interview Summary dated May 14, 2010, in U.S. Appl. No. 11/268,261.
Notice of Allowance dated Oct. 8, 2010, in U.S. Appl. No. 11/268,261.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 26, 2010 in U.S. Appl. No. 11/942,673.
Interview Summary dated Jul. 26, 2010 in U.S. Appl. No. 11/942,673.
NonFinal Office Action dated Sep. 16, 2010 in U.S. Appl. No. 11/942,687.
Non-Final Office Action dated Sep. 29, 2010 in U.S. Appl. No. 11/944,000.
Interview Summary dated May 31, 2011 in U.S. Appl. No. 12/702,976.
Notice of Allowance dated Jul. 20, 2011, in U.S. Appl. No. 12/702,976.
Office Action dated May 16, 2011, in U.S. Appl. No. 12/857,915.
Interview Summary dated Sep. 6, 2011, in U.S. Appl. No. 12/857,915.
Notice of Allowance dated May 26, 2011 in U.S. Appl. No. 11/265,979.
Non-Final Office Action dated May 5, 2011 in U.S. Appl. No. 12/870,645.
Interview Summary dated Jun. 7, 2011 in U.S. Appl. No. 11/944,000.
Interview Summary dated Dec. 1, 2010, in U.S. Appl. No. 12/702,976.
Final Office Action dated Feb. 17, 2011 in U.S. Appl. No. 12/702,976.
Notice of Allowance dated Dec. 3, 2010 in U.S. Appl. No. 11/268,261.
Notice of Allowance dated Jan. 6, 2011, in U.S. Appl. No. 11/268,261.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Interview Summary dated Dec. 3, 2010 in U.S. Appl. No. 11/942,687.
Final Office Action, dated Apr. 5, 2011 in U.S. Appl. No. 11/942,687.
Final Office Action dated Apr. 20, 2011 in U.S. Appl. No. 11/944,000.
Notice of Allowance dated May 17, 2010, in U.S. Appl. No. 11/268,261.
Supplemental Notice of Allowance dated Aug. 6, 2010, in U.S. Appl. No. 11/268,261.
Final Office Action dated Oct. 12, 2012 in U.S. Appl. No. 13/171,081.
Interview Summary dated Nov. 6, 2012 in U.S. Appl. No. 13/171,081.
Non-Final Office Action dated Apr. 4, 2013 in U.S. Appl. No. 13/535,758.
Notice of Allowance, dated Feb. 6, 2013, in U.S. Appl. No. 13/118,085.
Notice of Allowance dated Oct. 15, 2012 in U.S. Appl. No. 12/622,404.
Office Action dated Mar. 4, 2013 in U.S. Appl. No. 12/891,543.
Interview Summary dated Apr. 5, 2013 in U.S. Appl. No. 12/891,543.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Final Office Action dated Dec. 15, 2011, in U.S. Appl. No. 12/857,915.
Office Action dated Jun. 12, 2012, in U.S. Appl. No. 12/857,915.
Office Action dated Jun. 8, 2012 in U.S. Appl. No. 13/171,081.
Interview Summary dated Jul. 31, 2012 in U.S. Appl. No. 13/171,081.
Non-Final Office Action dated Jan. 11, 2012 in U.S. Appl. No. 13/079,597.
Notice of Allowance dated Apr. 25, 2012, in U.S. Appl. No. 13/079,597.
Non Final Office Action Dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Mendelson, et al., "Informatics in Radiology—Image Exchange: IHE and the Evolution of Image Sharing," RadioGraphics, Nov.-Dec. 2008, vol. 28, No. 7.
US 7,801,341, 09/2010, Fram et al. (withdrawn)
US 8,208,705, 06/2012, Reicher et al. (withdrawn)

* cited by examiner

ATTRIBUTES

| | 301 CONSENT | 302 REFERRAL | 303 SCREENING | 304 REGISTRATION | 305 EXAM | 306 ID | | | |
|---|---|---|---|---|---|---|---|---|---|
| 312 → SECURITY | C | O | M | M | M | C | o | o | o |
| 314 → LINKS | | | Link -> M | | | | o | o | o |
| 316 → SERIES | CNST | REFL | SCRN | RGST | EXM | ID | o | o | o |
| 318 → FILE TYPE | DOC | DOC | DOC | DOC | IMG | IMG | | | |

310

Legend

| | |
|---|---|
| O | Open |
| C | Confidential |
| M | Medical |
| Link -> M | Link to Medical Images |
| CNST | Consent Form |
| REFL | Referral Form |
| SCRN | Screening Form |
| RGST | Registration Form |
| EXM | Exam Form |
| ID | Patient Identification |
| IMG | Medical Image |
| DOC | Medical Document |

AUTOMATED DOCUMENT FILING

CROSS-REFERENCE TO RELATED APPLICATIONS

This application claims the benefit of U.S. Provisional Application No. 60/867,071, filed Nov. 22, 2006, which is hereby incorporated by reference in its entirety herein.

BACKGROUND OF THE INVENTION

1. Field of the Invention

The invention relates to management of medical forms.

2. Description of the Related Art

Medical documents are often scanned and processed into an electronic format for easy filing and recording of a patient's medical history. These medical documents encompass a variety of medical forms, such as medical registration forms, consent forms, and screening forms, for example. Depending on the type of medical document, the documents may have different user access rights, security rights, and modes of display.

SUMMARY OF THE INVENTION

In one embodiment, a computerized method of assigning attributes to medical forms comprises receiving an electronic copy of a form associated with a patient, determining one or more form types associated with the medical form from a plurality of form types, the plurality of form types comprising one or more of referral, medical record release, consent, and screening, accessing an attribute data structure comprising indications of each of the plurality of form types and one or more attributes associated with each respective form type, selecting attributes of the attribute data structure associated with the determined one or more form types, and storing the electronic copy of the form in a storage location associated with one or more of the selected attributes.

In one embodiment, a computerized system of organizing medical forms completed by a plurality of patients comprises a storage device storing an attribute data structure comprising indications of attributes associated with respective medical form types, the attributes comprising at least a security attribute and a document type attribute for each of the medical form types, an input interface configured to receive a digital representation of a medical-related form, the medical-related form comprising information associated with a patient, and a document management module configured to determine one or more form types associated with the medical-related form and to store the digital representation of the medical-related form with data indicating the attributes from the attribute data structure associated with the determined one or more form types.

In one embodiment, a computer-readable storage medium comprises software code configured to perform the method of storing a data structure on a storage device, the data structure comprising an indication of one or more document types and one or more attributes that are associated with respective of the document types, receiving an indication of a document type associated with an electronic document, selecting one or more attributes associated with the indicated document type in the data structure, and associating the selected one or more attributes with the electronic document.

In one embodiment, a computerized method of viewing medical forms comprises receiving an indication of an electronic form that a user of a computing system desires to view, accessing attribute data associated with the electronic form, the attribute data comprising at least a security attribute and a document type attribute, determining one or more display parameters for viewing the electronic form based on the attribute data, and generating a user interface comprising a depiction of the electronic form according to the determined display parameters.

BRIEF DESCRIPTION OF THE DRAWINGS

FIG. 3 illustrates an attribute data structure comprising data that indicates associations between respective series and their corresponding attributes.

FIG. 7 is one embodiment of a graphical user interface that may be used to select electronic documents and assign series attributes to the selected documents.

DETAILED DESCRIPTION OF CERTAIN EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

As used herein, the terms "medical forms," "forms," and "documents" are defined to include any forms related to medical information, images, and patient information. As non-limiting examples, the terms may include, but are not limited to, image screening forms, patient information forms, insurance information forms, information forms for respective exam types, consent forms, and many other types of medical-related forms. Medical forms may be hard copy forms and/or electronic forms of various formats, such as PDF, DOC, XLS, HTML, XML, and various other formats.

As used herein, the terms "series type," "series," and "document type" are used to describe a category of forms. In one embodiment, a series is representative of the subject matter of forms associated with the series, such as screening, registration, and/or consent forms. In other embodiments, a series associated with a document indicates other characteristics of the document, such as a form provider or medical facility.

As used herein, the term "attribute" includes, but is not limited to an indicator of a characteristic of each form in of a respective series. In one embodiment, each series is associated with one or more attributes, and the attributes of a respective series are associated with documents in the respective series. Series attributes may comprise information indicating a security level associated with a document, a storage location of a document, a viewer associated with a document, a link to another related document, and/or a document type of a document. Depending on the embodiment, attributes may include indications of other characteristics of forms and/or the information contained in the forms.

Document Management

Figure 1A:
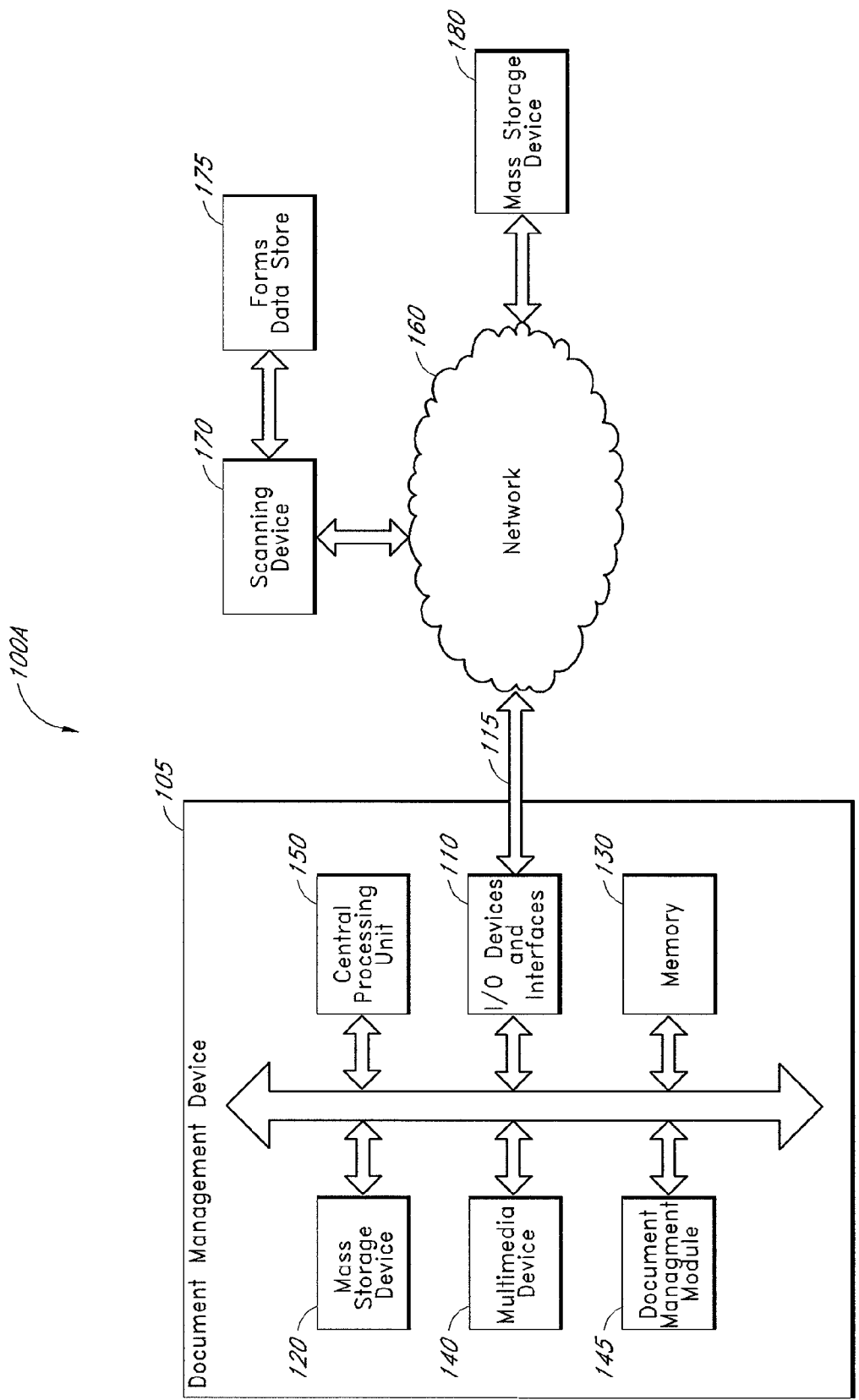
FIG. 1A is a block diagram of a computing system comprising a document management device in communication with a network and various networked devices.

FIG. 1A is a block diagram of a computing system 100A comprising a document management device 105 in communication with a network 160 and various networked devices. The computing system 100A may be used to implement certain systems and methods described herein. Depending on the embodiment, the functionality described below with reference to certain components and modules of the computing system 100A may be combined into fewer components and modules or further separated into additional components or modules.

The exemplary document management device 105 comprises a memory 130, such as random access memory (RAM) for temporary storage of information and a read only memory (ROM) for permanent storage of information, and a mass storage device 120, such as a hard drive, diskette, or optical media storage device. The mass storage device 120 may comprise one or more hard disk drive, optical drive, networked drive, or some combination of various digital storage systems. The document management device 105 also comprises a central processing unit (CPU) 150 for computation. Typically, the modules of the document management device 105 are in data communication via one or more standards-based bus system. In different embodiments, the standards based bus system could be Peripheral Component Interconnect (PCI), Microchannel, SCSI, Industrial Standard Architecture (ISA) and Extended ISA (EISA) architectures, for example.

The document management device 105 is generally controlled and coordinated by operating system software, such as the Windows 95, 98, NT, 2000, XP, Vista, or other compatible operating systems. In Macintosh systems, the operating system may be any available operating system, such as Mac OS X. In other embodiments, the document management device 105 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary document management device 105 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images and/or medical forms may be displayed. The document management device 105 may also include one or more multimedia devices 140, such as speakers, video cards, graphics accelerators, and microphones, for example.

In the embodiment of FIG. 1A, the I/O devices and interfaces 110 provide a communication interface to various external devices. In the embodiment of FIG. 1A, the document management device 105 is in data communication with a network 160, such as a LAN, WAN, or the Internet, for example, via a communication link 115. The network 160 may be coupled to various document management devices and/or other electronic devices. In the exemplary embodiment of FIG. 1A, the network 160 is in data communication with a forms data store 175, a scanning device 170, and a mass storage device 180. In other embodiments, the scanning device 170 may be locally coupled to the document management device 105. In addition to the devices that are illustrated in FIG. 1A, the network 160 may facilitate communications with other computing, imaging, and storage devices.

The forms data store 175 comprises a plurality of hardcopy and/or electronic documents, some of which comprise user editable fields configured to receive patient information. Patients may be asked to complete one or more forms that ask for patient biographical information, insurance information, exam information (e.g. exam modality), consent, or other information. Exemplary forms may include a radiology screening form, a patient information form, an insurance information form, an exam type form, various patient consent forms, and many other types of medical forms.

The scanning device 170 comprises an electronic device that digitizes a form from the forms data store 175. Exemplary scanning devices may include a flatbed scanner, a hand scanner, or a drum scanner. In one embodiment, the scanning device 170 may comprise optical character recognition (OCR) software to translate images of handwritten or typewritten text into machine-editable text. In another embodiment, the scanning device 170 may analyze and decode document type indicators on scanned documents, such as a barcode that indicates a document type. As noted below, in certain embodiments forms may be electronic such that the scanning device 170 may not be necessary.

In one embodiment, the mass storage device 120, 180 may be any device that electronically stores information. Exemplary devices include, but are not limited to a hard disk drive, a flash memory based drive, a thumb drive, and disc-based storage mediums, such as a CD or DVD, for example. In one embodiment, these devices may be networked in series or in parallel with each other and may comprise storage area networks (SAN) for networking with the document management device 105. Depending on the embodiment, the mass storage device 120, 180 may comprise redundant array of independent drives (RAID) for increased data reliability or I/O performance, or both.

In the embodiment of FIG. 1A, the document management module 145 is configured to associate series attributes with one or more electronic documents, such as scanned documents or electronically completed documents. In one embodiment, the document management module 145 provides a user interface that may be used to provide an indication of one or more series associated with an electronic document. In another embodiment, this module receives information regarding document attributes from another source. In other embodiments, the document management module 145 comprises document detection intelligence that determines a type of document and/or series for an electronic document. After determining a series associated with a document, the document management module 145 determines attributes for the determined series and associates those attributes with the electronic document. The document attributes associated with the electronic document may then be used to control user's rights to the document, indicate a type of viewer associated with the document, indicate a storage location for the document, indicate a type of the electronic document, and/or indicate when a document is to be stored (such as differentiating forms that require user completion from those that are stored with a patient's record without first requiring completion), for example.

Figure 1B:
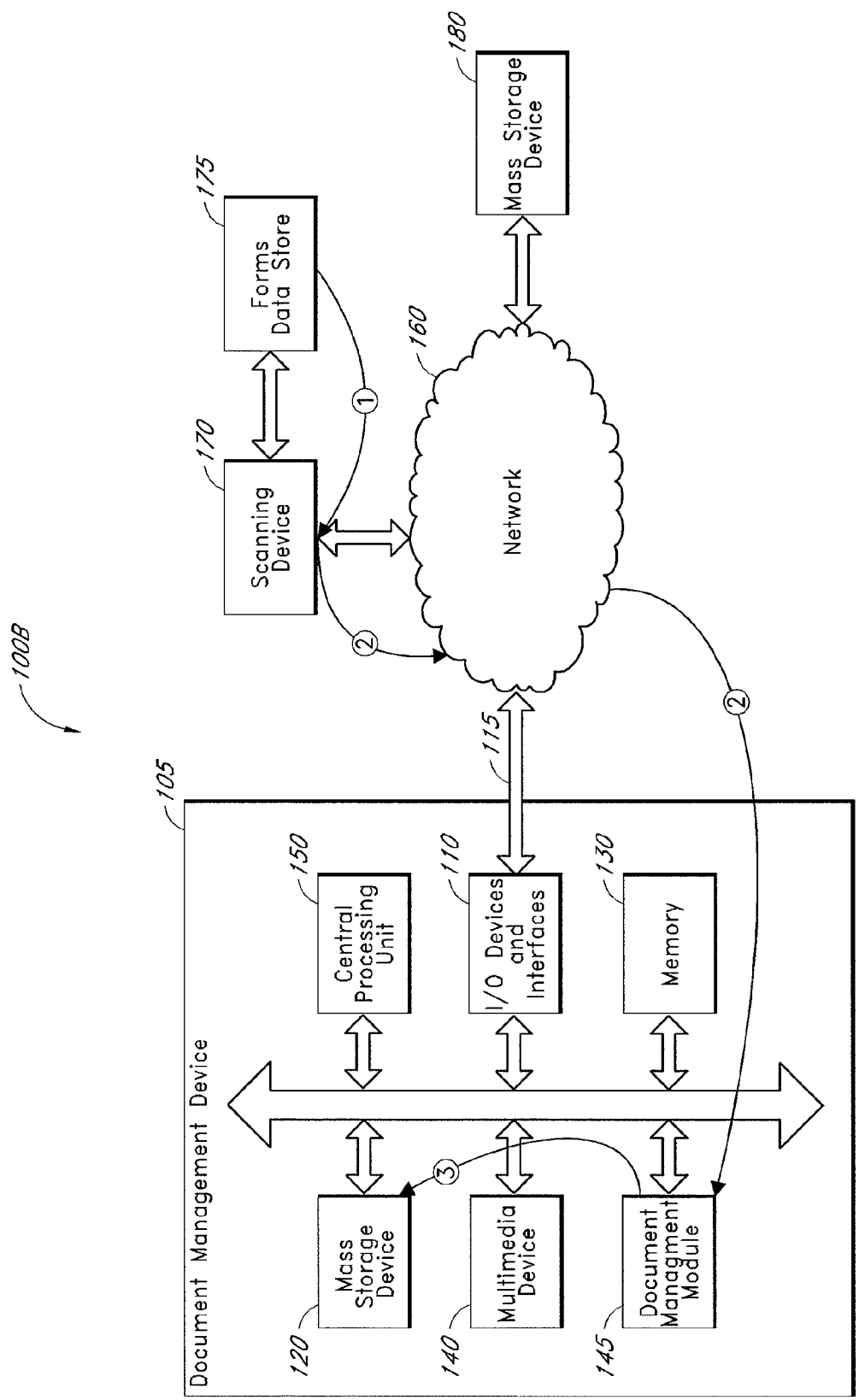
FIG. 1B is a block diagram illustrating one embodiment of a computing system comprising a document management device in communication with a network and various networked devices.

FIG. 1B is a block diagram illustrating one embodiment of a computing system 100B comprising a document management device 105 in communication with a network 160 and various networked devices. The computing system 100B may be used to implement certain systems and methods described herein. In the embodiment of FIG. 1B, an exemplary temporal flow of operations is indicated by the circled numerals 1-3 and is described in further detail below. Depending on the embodiment, certain steps may be removed and additional steps may be added.

In step one of FIG. 1B, the scanning device 170 receives and scans one or more physical documents from the forms data store 175 in order to convert the physical documents into corresponding electronic documents. For example, the scanning device 170 may receive a plurality of forms on a sheet-feeder, scan the forms, and create digital representations of the scanned forms in one or more of many available digital formats, including PDF, PNG, JPG, GIF, and TIFF, for example.

In another embodiment, the forms data store 175 comprises electronic forms comprising medical-related information that do not require scanning. In this embodiment, the forms data store 175 may be accessed directly by the document management device 105, such as via the network 160 or a local area network, for example.

In step two of FIG. 1B, the electronic documents, or at least a representation of the electronic documents, are accessible by the document management device 105. The document management module 145 may then receive or determine a series of each electronic document so that attributes of the determined series may be associated with the document. In one embodiment, a user of the document management module 145 views at least a portion of the electronic documents in order to determine a series of respective documents. The user may then select one or more series via a user interface provided by the document management device 105. In another embodiment, the document management module 145 and/or scanning device 170 are configured to determine a series of certain electronic documents based on a visual indicator of the electronic documents, such as a document title, header, footer, document number, etc. that are recognized in the electronic documents, such as by using OCR recognition of a scanned document.

In step three, the document management module 145 determines those attributes associated with the determined series of an electronic document and associates the series attributes with the specific document. In one embodiment, the document management module 145 accesses one or more data structures comprising associations between respective series and attributes, such as attributes indicating security/access rights, document type, viewer information, and/or form storage information, for example. The electronic document, along with the corresponding attributes, may then be stored in the mass storage device 120 and/or any other external storage device, such as the mass storage device 180 and/or a storage device of an electronic medical records ("EMR") system (not shown), for example.

Figure 2:
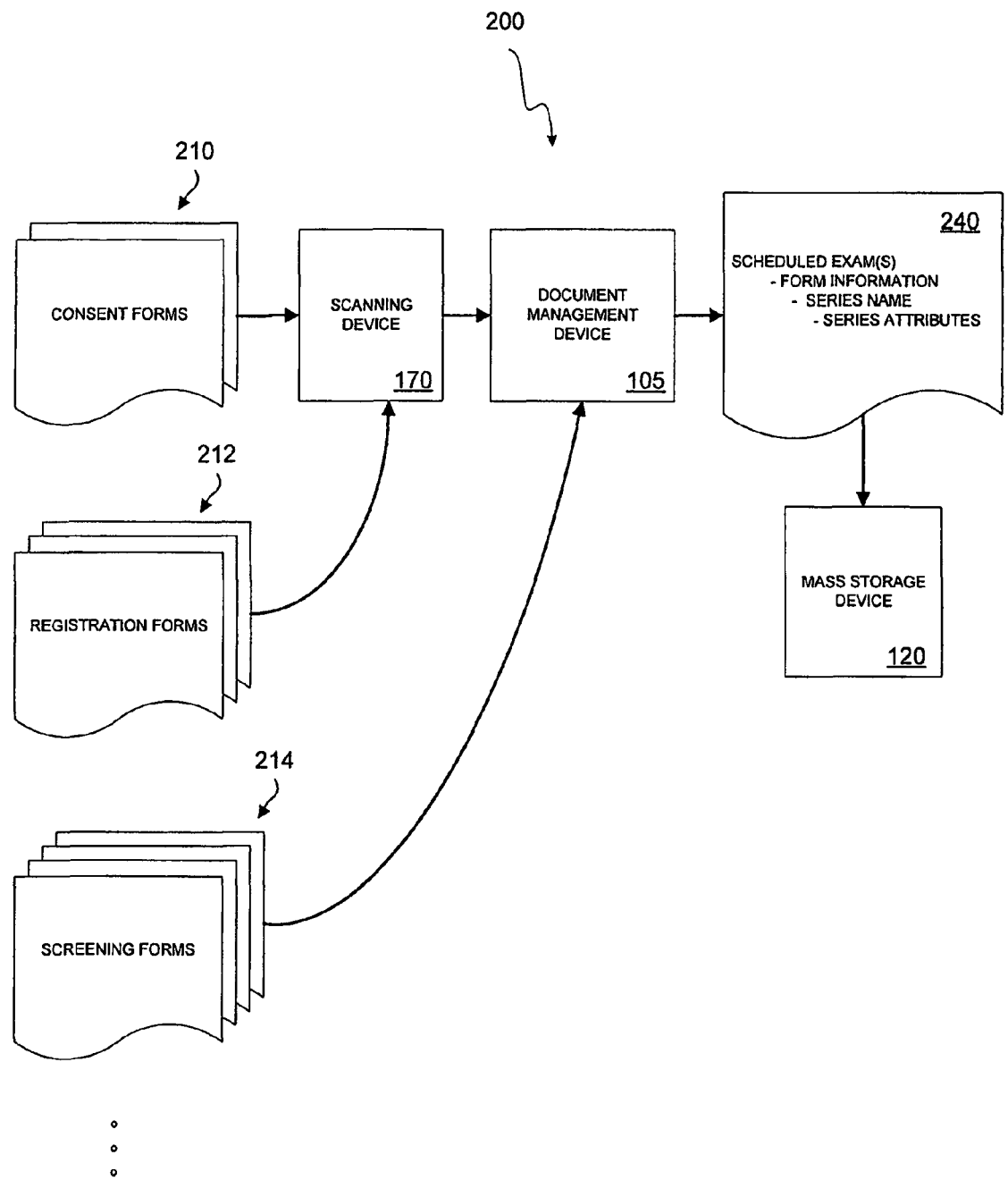
FIG. 2 is a data flow chart illustrating the movement of physical and electronic documents through a document management system.

FIG. 2 is a data flow chart 200 illustrating the movement of physical and electronic documents through a document management system. Starting from the scanning device 170 in FIG. 2, physical forms 210 and 212 are scanned into an electronic format and sent to, or otherwise accessed by, the document management device 105. In the embodiment of FIG. 2, the screening forms 214 comprise electronic forms that are directly transmitted to, or otherwise accessed by, the document management device 105, such as via a local and/or network connection to the document management device 105.

When the document management module 145 has received an electronic form, the document management module 145 associates attributes to the form that direct further automated storage and display rules. For example, a user of the document management device 105 may view at least a portion of the form in a user interface provided by the device 105 and make a determination as to a "series" associated with the form. When the form is included in a particular "series", the attributes of that series can determine how the form is stored, when it is stored, how it is displayed, and/or it's level of security, for example. Alternatively, the device 105 may automatically associated attributes to the form based on one or more visually detectable characteristics of the form. Advantageously, certain series are associated with one or more attributes so that forms in a particular series may inherit the attributes of that particular series. As discussed above, series attributes may indicate a document type, a link to another documents, and/or a security level of a particular document. The form attributes may be included in a header portion of the digital file or a separate file associated with the digital file, for example.

Form 240 of FIG. 2 illustrates exemplary attribute information that may be associated with the electronic document. As illustrated in FIG. 2, the form 240 is associated with a scheduled exam, which may include various types of patient information, such as patient name, address, contact information, medical record number, social security number, etc. In other embodiments, the form 240 is not associated with a particular exam, but is generally associated with a patient, such as via a patient identification number or social security number. The form 240 also includes an indication of the series to which the form has been associated, e.g., either automatically by the document management device 105 or manually by a user viewing at least a portion of the form. The form 240 also includes zero or more attributes associated with the form, such as those attributes that are automatically associated with the form based on an indicated series of the form. In one embodiment, the series name is not include as part of the form information; instead, only the attributes associated with the form's series are assigned to the form.

After associating the appropriate attributes to the digital forms 210, 212, 214, the forms may be stored in one or more data stores, such as the mass storage device 120, 180. In one embodiment, the processed forms may be stored in one or more folders based on one or more of the attributes. For example, one or more attributes may indicate a folder to which a corresponding form should be stored. In this embodiment, all of the forms in a particular series may be automatically stored in a series-specific folder. In one embodiment, a patient's medical records comprises folders for certain forms, such as a consent folder for storage of executed consent forms. By accessing the document type attribute of forms, consent forms may be identified and the document management module 145 may be configured to automatically move the consent form to the consent folder for the corresponding patient.

FIG. 3 illustrates an attribute data structure 310 comprising data that indicates associations between respective series and their corresponding attributes. In one embodiment, the document management module 145 may determine attributes to associate with a particular form by accessing the data structures 310. FIG. 3 also illustrates a legend 320 that indicates the meaning of symbols used in the data structure 310. Although exemplified in the form of a table, the intent is not to limit the data structure that may be employed to create associations or links between forms, attributes, and other links to such various items as exam types, facilities, insurance information, for example.

The exemplary data structure 310 comprises attribute data associated with six exemplary series. More particularly, the data structure 310 comprises a consent series column 301, a referral series column 302, a screening series column 303, a registration series column 304, an exam series column 305, and an identification series column 306. Each of the series may be associated with one or more attributes, such as security attributes indicated in row 312, link attributes in row 314, series type attributes in row 316, and/or file type attributes in row 318. For example, the exemplary data structure 310 indicates that documents in the referral series should be associated with an open security level, a REFL symbol indicating that the document is a referral document, and that the documents are medical documents (rather than medical images). In one embodiment, the file type of a form (e.g., row 318) indicates a particular viewer or class of viewer that is used by a viewer of the form. For example, medical documents may be opened in a first viewer, such as a word processing or portable document viewer, and medical images may be opened in a second viewer, such as a viewer of radiology imaging software. Depending on the embodiment, the data structure 310 may comprise additional series attributes and/or different attributes associated with respective series. For example, additional attributes may include information regarding image size and image resolution, for example.

FIG. 3 illustrates three security attributes, namely, open, confidential, and medical. Depending on the embodiment, fewer or additional security attributes may be associated with forms. In one embodiment, the open security level indicates that an associated document may be viewed by any user of the system, including clerical workers and medical professionals; the confidential security level indicates that viewers with a confidential clearance may view the document; and the medical security level indicates that only medical personnel, such as a family doctor may view the document.

The exemplary data structure 310 indicates a link attribute for screening series 303. In one embodiment, link attributes are used to associate two or more types of forms and or specific forms. Using a link attribute may enable form(s) related to a requested form to be automatically opened in response to a link attribute associated with a requested form. In one embodiment, when two or more forms are linked together, both forms may be viewed at the same time when either form is selected. For example, it may be advantageous to have a patient screening form linked to medical images associated with a scheduled exam, so that when the patient screening form is accessed the medical images are opened, listed for easy access by the user, or otherwise brought to the attention of the user.

The file type attributes of FIG. 3 include medical document (DOC) and medical image (IMG) file types. In one embodiment, files of the same file type are filed in the same folder on the mass storage device 120, 180. For example, medical documents and medical images for a particular scheduled exam may be filed in separate folders. In one embodiment, a patient's scheduled exam may include a plurality of files and each of the files may be sorted and stored in different folder structures depending on the document type of the files(s).

In one embodiment, document types and/or other attributes of a document may indicate a mode of display. For example, certain types of documents may be displayed in a new display container to illustrate and isolate particular features of the document without interrupting the user's eyes from viewing something else, while other types of documents are opened in a currently active display container.

Figure 4:
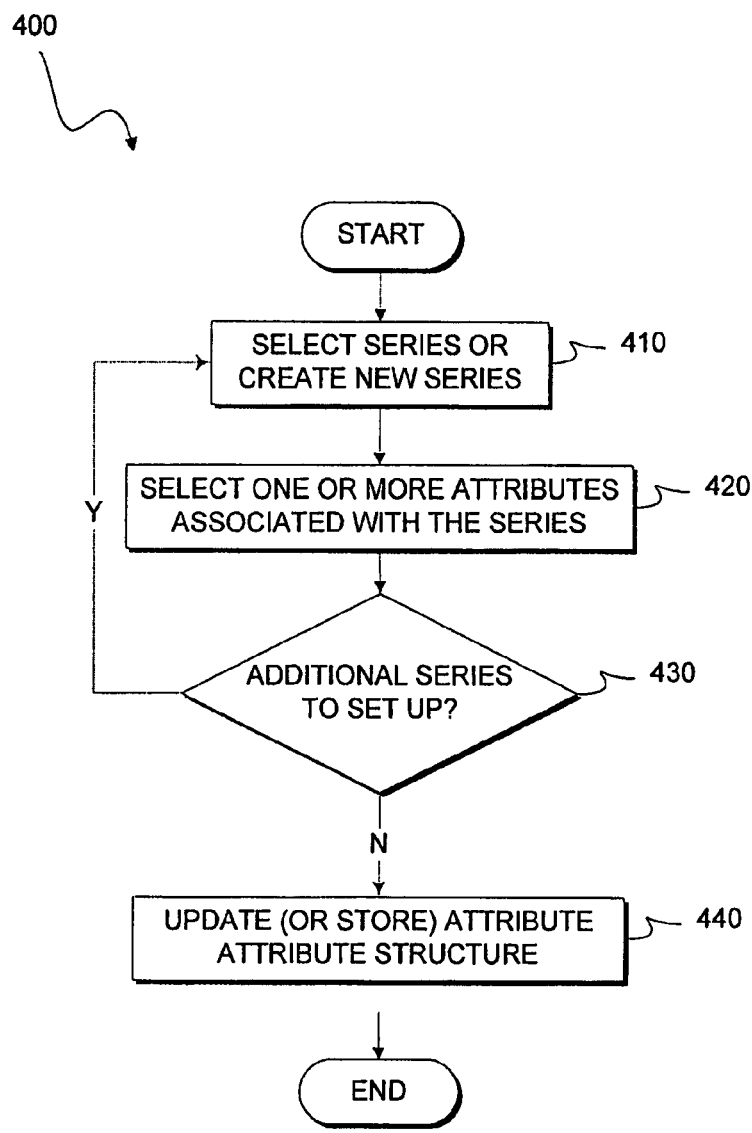
FIG. 4 is a flowchart illustrating one embodiment of a method of establishing attributes associated with respective series.

FIG. 4 is a flowchart illustrating one embodiment of a method of establishing attributes associated with respective series. In one embodiment, the method of FIG. 4 is performed by an administrator that has rights to establish new series and/or attributes associated with existing series. For example, a user interface may be presented to the administrator in order to allow selection of attributes for association with respective series. Depending on the embodiment, the method of FIG. 4 may include fewer or additional blocks, and the blocks may be performed in a different order than as illustrated.

Beginning in block 410, an existing series is selected or a new series is created. For example, the user may create a consent series that is associated with attributes that should be associated with consent forms. Alternatively, the user may select an existing series that may already have one or more associated attributes so that the attributes that are currently associated with the series may be edited.

Next, in block 420 one or more attributes to be associated with the selected series (block 410) are selected by the user. For example, the user may select one or more of a security, link, series, file storage location, file type, and/or any other available attribute to be associated with the selected series. Depending on the embodiment, other attributes may also be available for selection in block 420.

Moving to block 430, the user determines if additional series are to be set up and/or modified to be associated with different attributes. If additional series are to be added and/or modified, the method returns to blocks 410 and then 420.

In block 440, the attributes associated with respective series (e.g., blocks 410-430) are stored in an attribute data structure. As discussed above, the attribute data structure may be accessed by the document management module 145 in order to determine attributes to be associated with a particular electronic document, such as a scanned form.

Figure 5:
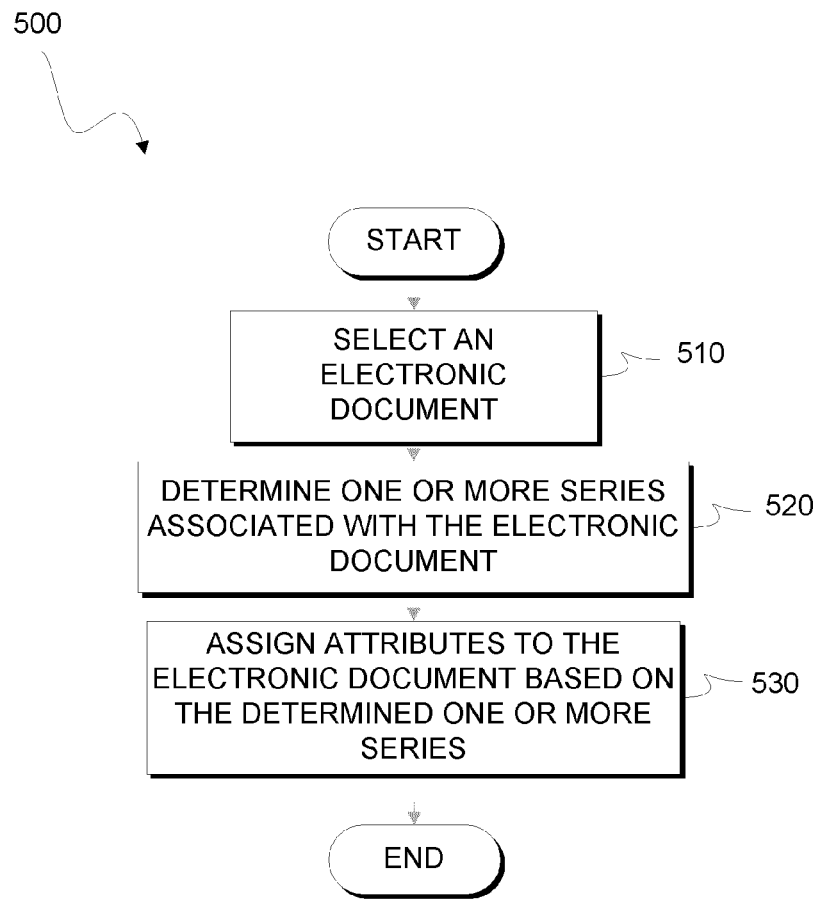
FIG. 5 is a flow chart illustrating one embodiment of a method of assigning attributes to electronic documents.

FIG. 5 is a flow chart illustrating one embodiment of a method of assigning attributes to electronic documents. Depending on the embodiment, the method of FIG. 5 may include fewer or additional blocks and the blocks may be performed in a different order than illustrated.

Beginning in block 510, an electronic document is selected. Selection of an electronic document may comprise selecting an electronic document from a list of electronic documents, such as in a folder of an electronic file structure. Alternatively, selection of an electronic document may comprise scanning a physical document such that a representation of at least a portion of the scanned document is presented to the user in a user interface. In other embodiments, electronic documents may be selected from other sources, such as a networked mass storage device or an EMR system. In one embodiment, batch processing may be used to select a series of electronic documents.

Moving to block 520, the document management module 145 determines one or more series that are associated with the electronic document. In one embodiment, a user of the document management device 105 selects the one or more series associated with the selected electronic document. In one embodiment, a list of available series are presented to the user and the user selects one or more series using an input device, such as a keyboard and/or mouse. In other embodiments, one or more series may be selected using any other means. In one embodiment, a series may be associated with only a single electronic document, while in other embodiments a series may be associated with a group of electronic documents. In another embodiment, the document management system 105 may analyze and decode series indicators on the electronic document, such as a barcode that indicates a series type.

Next, in block 530, the document management module 145 accesses the attribute data structure in order to determine one or more attributes to be associated with the electronic document. The document manager module 145 then associates the appropriate attributes to the electronic document so that the attributes are accessible to authorized users subsequently requesting access to the electronic document. For example, if the user selects the referral series in block 520, those attributes associated with the referral series are associated with the electronic document. In one embodiment, the attributes are stored in a header portion of the electronic document. In another embodiment, the attributes are stored in an index comprising an indication of the electronic document and/or the electronic document storage location, as well as the attributes associated with the electronic document. In other embodiments, the attributes associated with an electronic document may be stored in any other suitable format, such as a separate file that is stored with the electronic document.

After associating attributes with the electronic document, the document may be filed in a specific folder based on one or more attributes of the document. These attributes may indicate that the electronic document should be stored in a particular folder associated with a particular patient and/or a particular scheduled exam of the patient.

Figure 6:
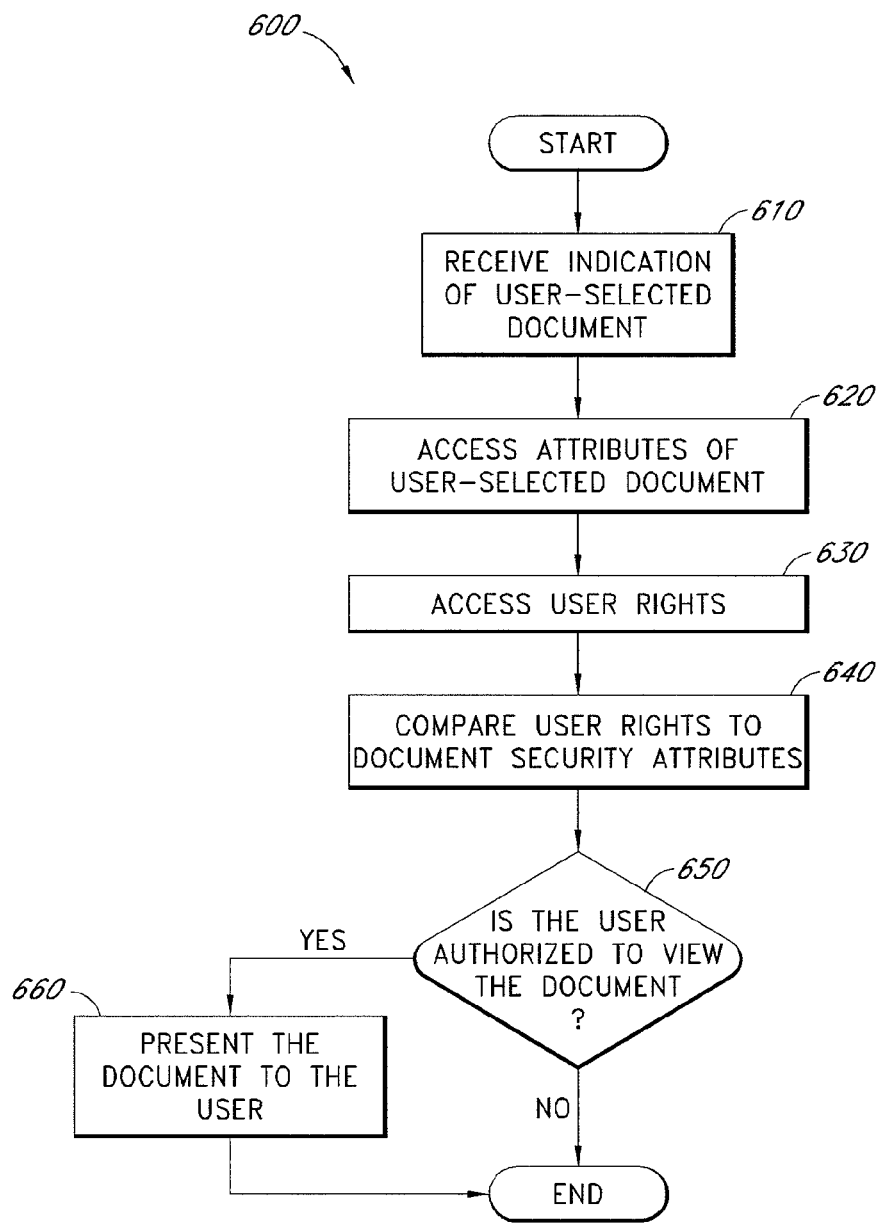
FIG. 6 is a flowchart illustrating one embodiment of a method of accessing an electronic document having associated attributes.

FIG. 6 is a flowchart illustrating one embodiment of a method of accessing an electronic document having associated attributes. Depending on the embodiment, the method of FIG. 6 may include fewer or additional blocks and the blocks may be performed in a different order than is illustrated.

Beginning in block 610, the document management device 105 receives an indication of a user selected document. For example, a user of the document management device 105 requests an electronic document for viewing via medical records software. Alternatively, a remote user, such as a user in communication with the document management device 105 via the network 160 may request access to a document stored on the document management device 105. In other embodiments, the documents and their associated attributes are stored remote to the document management device 105. In these embodiments, the indication of a user selected document may be received by a computing device that stores the particular requested document and/or controls access to the electronic documents. Thus, the method of FIG. 6 may be performed by the document management device 105 and/or by another computing device that controls access to electronic documents. For ease of description, the remaining description of FIG. 6 will be described with reference to the document management device 105, with the understanding that references to the document management device 105 should be interpreted to include actions that may be performed by other computing devices that control access to electronic documents.

Moving to block 620, the document management module 105 accesses the attributes of the user selected document. For example, the header information of the document may be accessed in order to determine attributes that are associated with a document.

Continuing to block 630, the requesting user's access rights are determined, such as via an access rights data structure indicating rights associated with respective users. For example, each user may be granted rights to one or more of open, confidential, and/or medical electronic documents.

In block 640, the user rights are compared to any security attributes associated with the electronic document.

Next, in block 650, the document management device 105 determines if the user is authorized to view the requested electronic document. In one embodiment, the determination is based on the comparison of user rights to document security attributes. For example, if the requesting user only has rights to view open electronic documents, the user may be denied access to confidential electronic documents. If the user is determined to have rights to view the requested document, the method continues to block 660 where the electronic document is transmitted to the user, or otherwise made accessible to the user. If, however, the user does not have rights to view the document, the user is not provided access to the electronic document.

Figure 7:
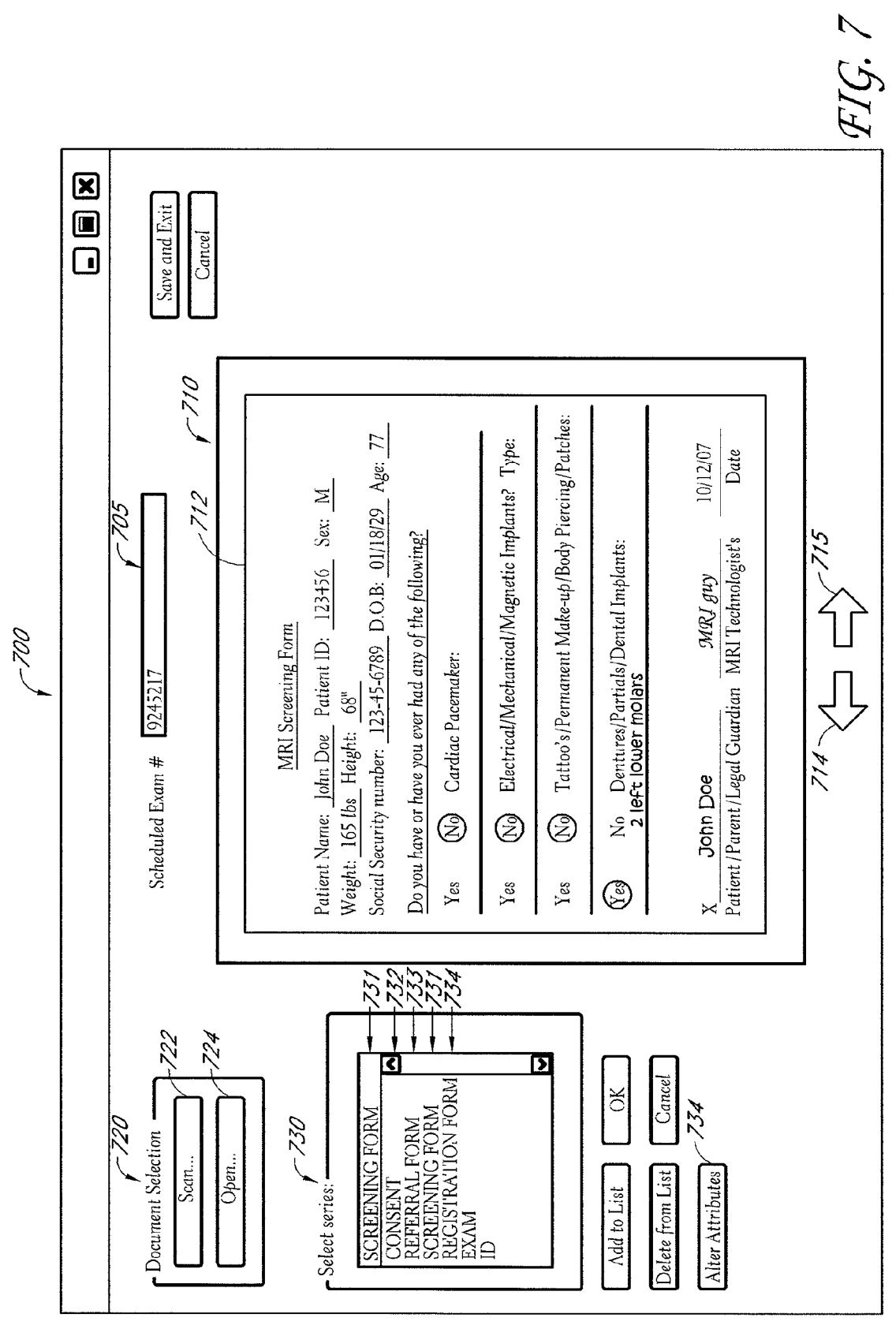

FIG. 7 is one embodiment of a graphical user interface 700 that may be used to select electronic documents and assign series attributes to the selected documents. The embodiment of FIG. 7 may be used to control operation of a scanner and to open electronic documents from a local or remote storage device. The exemplary graphical user interface 700 comprises a document preview pane 710, a document selection pane 720, a series selection pane 730, and a scheduled exam field 705. Depending on the embodiment, the layout of the graphical user interface, the types of input fields, buttons, and checkboxes may be modified.

The patient scheduled exam field 705 may be used to associate an electronic document displayed in preview pane 710 with a particular patient scheduled exam. As noted above, the patient scheduled exam may comprise the patient identification number and one or more attributes associated with the patient.

The document preview pane 710 may be used to view at least a portion of a selected electronic document. Thus, a user may better perceive the content of the selected electronic document by viewing at least a portion of the document in the preview pane 710. Arrows 714, 715 may be used to move to previous or next electronic documents in a directory of a storage device, such as a scanned images folder on a storage device, for example.

The document selection pane 720 may be used to select an electronic document for assigning attributes. In one embodiment, selecting button 724 displays options/parameters to select an electronic form residing on mass storage device 120, 180, while selecting button 722 may indicate that an electronic document should be acquired from a scanner, and may present the user with scanning parameters that may be adjusted prior to scanning documents.

In the embodiment of FIG. 7, the series selection pane 730 is used to select one or more series to be associated with the electronic document depicted in the document preview pane 710. Exemplary series selection pane 700 illustrates several series identifier that may be selected by the user in order to indicate one or more series attributes to be associated with the currently selected electronic document.

Exemplary user interface 700 further comprises an alter attributes button 734 that may be used to alter attributes associated with a series, such as adding and/or removing attributes associated with a series.

The foregoing description details certain embodiments of the invention. It will be appreciated, however, that no matter how detailed the foregoing appears in text, the invention can be practiced in many ways. For example, the above-described document management module 145 may be performed on other types of documents, in addition to medical forms. For example, educational forms and business documents may be analyzed using the described systems. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computerized method of assigning attributes to medical forms, the method comprising:
   receiving at a document management computing system, from an external source, an electronic medical form associated with a specific patient, wherein the received electronic medical form includes information regarding the specific patient including at least a last name of the specific patient, wherein the information was provided by the patient and/or determined based on personal information of the patient;
   determining a form type associated with the electronic medical form, wherein the form type is selected from a group comprising one or more of image screening forms, patient information forms, insurance information forms, information forms for respective exam types, consent forms, screening forms, registration forms, or referral forms;
   accessing, by the document management computing system, an attribute data structure comprising indications of each of a plurality of form types and associations between respective form types and one or more respective attributes;
   selecting, by the document management computing system, a storage location information attribute associated with the determined form type in the attribute data structure;
   associating the storage location information attribute with the electronic medical form; and
   initiating storage of the electronic medical form based on the storage location information attribute.

2. The method of claim 1, wherein the electronic medical form comprises a scanned document.

3. The method of claim 1, wherein the electronic medical form comprises an electronic document having one or more fields that are filled with electronic data.

4. The method of claim 1, further comprising:
   selecting, by the document management computing system, one or more other attributes associated with the determined form type in the attribute data structure; and
   storing the selected attributes associated with the determined form type.

5. The method of claim 4, further comprising:
   accessing the stored attributes;
   determining one or more display parameters for the electronic medical form based on one or more of the stored attributes; and
   displaying the electronic medical form according to the determined display parameters.

6. The method of claim 5, wherein the display parameters comprise one or more of a parameter indicating a window for viewing of the electronic medical form, a parameter indicating a viewer type, and a parameter indicating a required security level of a viewer that is required for viewing the electronic medical form.

7. The method of claim 5, wherein a type of viewing window for displaying the electronic medical form is selected based on the determined form type.

8. The computerized method of claim 1, wherein the storage location indicates a location relative to a storage location associated with the specific patient.

9. The computerized method of claim 1, wherein at least some attributes of forms may be determined based on respective storage locations of forms.

10. A computerized system of organizing medical forms, the system comprising:
    a storage device storing an attribute data structure comprising indications of attributes associated with respective medical form types, the attributes comprising at least a security attribute and a document type attribute for each of the medical form types;
    an input interface configured to receive a digital representation of a medical-related form, the medical-related form comprising information associated with a specific patient when received by the computerized system, wherein the information includes at least a last name of the specific patient; and
    a document management module configured to
       determine one or more form types associated with the medical-related form;
       determine one or more attributes in the attribute data structure that are associated with the determined one or more form types;
       generate data indicating the determined one or more attributes; and
       store the digital representation of the medical-related form with the data indicating the determined one or more attributes, wherein the determined one or more attributes includes at least a security attribute and a document type attribute.

11. The system of claim 10, wherein the document management module is further configured to store the digital representation of the medical-related form in a storage location associated with the determined document type attribute so that forms of the same document type are stored at common storage locations.

12. The system of claim 10, wherein the document management module is further configured to present the digital representation of the medical-related form in a viewer that is selected based on the determined document type attribute associated with the digital representation of the medical-related form.

13. The system of claim 10, wherein the data indicating the determined one or more attributes is stored in a header portion of the digital representation of the medical-related form.

14. The system of claim 10, wherein the document management module analyzes at least a portion of the digital representation of the medical-related form in order to determine one or more form types associated with the medical-related form.

15. The system of claim 12, wherein the at least a portion of the digital representation of the medical-related form comprises a bar code.

16. The system of claim 10, wherein the document management module determines the one or more form types based on information provided by a user of the computerized system.

17. A non-transitory computer-readable storage medium storing software code configured for execution by a computing device in order to perform operations comprising:
    accessing a data structure on a storage device, the data structure comprising an indication of one or more document types and one or more attributes that are associated with respective of the document types;
    receiving an indication of a document type associated with an electronic document comprising information identifying a specific patient;

selecting one or more attributes associated with the indicated document type in the data structure, wherein one of the attributes indicates a storage location for the indicated document type;

associating the selected one or more attributes with the electronic document; and initiating storage of the electronic document at the storage location for the indicated document type.

18. The non-transitory computer-readable storage medium of claim 17, wherein the selected one or more attributes indicate one or more of: a storage location, a document type, a security level, and an associated file type.

19. The non-transitory computer-readable storage medium of claim 17, wherein the indication of the document type is received from a user-controlled input device.

20. The non-transitory computer-readable storage medium of claim 17, wherein the indication of the document type is received from software means configured to determine a document type based on one or more characteristics of the electronic document.

21. The non-transitory computer-readable storage medium of claim 18, wherein characteristics of the electronic document comprise file size, file name, text of the electronic document, images in the electronic document, barcodes or other unique codes associated with the electronic document.

22. A computerized method of viewing medical forms, the method comprising:

by a computing device including hardware:

receiving a selection of an electronic form that a user of a computing system desires to view, wherein the selected electronic form includes information regarding a particular patient;

determining a type of the electronic form, wherein the type of the electronic form includes one or more of an image screening form, a patient information form, an insurance information form, an information form for a particular exam type, a consent form, a screening form, a registration form, or a referral form;

accessing attribute data associated with the determined type of the electronic form, the attribute data comprising at least a security attribute for the determined type of electronic form;

determining one or more user attributes associated with the user of the computing system; and based on at least the security attribute for the determined type of electronic form and the one or more user attributes, determining one or more display parameters for depicting the electronic form for viewing by the user of the computing system.

23. The computerized method of claim 22, wherein the attribute data further comprises a document type attribute, wherein the document types comprise an image type and a non-image type.

24. The computerized method of claim 22, wherein the user attributes must be included in a predefined group of user attributes associated with the security attribute in order for the user to view the electronic document.

25. The computerized method of claim 23, further comprising initiating execution of an image viewer in response to determining that a document type attribute associated with the electronic form indicates a first type of document.

26. The computerized method of claim 22, further comprising generating a user interface comprising a depiction of the electronic form according to the determined display parameters.

27. The computerized method of claim 26, wherein the user interface comprises a new window for displaying the electronic document in response to determining that the document type indicates a second type of document.

28. A non-transitory computer-readable storage medium comprising software code configured for execution by a computing device in order to perform operations comprising:

receiving an indication of a specific document type;

accessing a data structure comprising an indication of document types and one or more attributes that are associated with respective of the document types;

selecting one or more attributes associated with the received document type in the data structure, wherein one of the attributes indicates storage location information for documents of the received document type;

generating an instance of the specific document type;

determining a specific patient associated with the instance of the specific document type;

associating the specific patient and the selected one or more attributes with the instance of the specific document type; and generating an indicator specific to the instance of the specific document type.

29. The non-transitory computer-readable storage medium of claim 28, wherein the indicator comprises a barcode.

* * * * *

UNITED STATES PATENT AND TRADEMARK OFFICE
CERTIFICATE OF CORRECTION

Page 1 of 1

| | |
|---|---|
| PATENT NO. | : 8,554,576 B1 |
| APPLICATION NO. | : 11/944027 |
| DATED | : October 8, 2013 |
| INVENTOR(S) | : Reicher et al. |

It is certified that error appears in the above-identified patent and that said Letters Patent is hereby corrected as shown below:

In the Drawings

Sheet 1 of 18 (FIG. 1A) at line 2 (Reference numeral 145), Change "Managment" to --Management--.

Sheet 2 of 18 (FIG. 1B) at line 2 (Reference Numeral 145), Change "Managment" to --Management--.

In the Specification

In column 7 at line 44, Change "and or" to --and/or--.

In the Claims

In column 13 at line 22, In Claim 21, Change "claim 18" to --claim 20--.

Signed and Sealed this
Twentieth Day of May, 2014

Michelle K. Lee
*Deputy Director of the United States Patent and Trademark Office*